(12) United States Patent
Johnson et al.

(10) Patent No.: US 7,438,924 B2
(45) Date of Patent: *Oct. 21, 2008

(54) DRY GRANULATED FORMULATIONS OF AZITHROMYCIN

(75) Inventors: Barbara A. Johnson, Niantic, CT (US); Ernest S. Quan, East Lyme, CT (US)

(73) Assignee: Pfizer Inc, New York, NY (US)

( * ) Notice: Subject to any disclaimer, the term of this patent is extended or adjusted under 35 U.S.C. 154(b) by 863 days.

This patent is subject to a terminal disclaimer.

(21) Appl. No.: 10/355,575

(22) Filed: Jan. 31, 2003

(65) Prior Publication Data

US 2003/0228357 A1    Dec. 11, 2003

Related U.S. Application Data

(60) Provisional application No. 60/354,041, filed on Feb. 1, 2002.

(51) Int. Cl.
*A01N 25/34* (2006.01)
*A61K 31/70* (2006.01)

(52) U.S. Cl. .................... 424/408; 514/29; 536/7.4

(58) Field of Classification Search ............. 424/408; 514/29; 536/7.4
See application file for complete search history.

(56) References Cited

U.S. PATENT DOCUMENTS

| | | | |
|---|---|---|---|
| 4,474,768 A | 10/1984 | Bright | 424/180 |
| 4,963,531 A | 10/1990 | Remington | 514/29 |
| 5,605,889 A | 2/1997 | Curatolo et al. | 514/29 |
| 5,633,006 A | 5/1997 | Catania et al. | 424/441 |
| 6,068,859 A | 5/2000 | Curatolo et al. | 424/490 |
| 6,245,903 B1* | 6/2001 | Karimian et al. | 536/7.4 |
| 6,268,489 B1 | 7/2001 | Allen et al. | 536/7.4 |
| 6,339,063 B1 | 1/2002 | Kropp et al. | 514/29 |
| 6,365,574 B2* | 4/2002 | Singer et al. | 514/29 |
| 6,764,997 B2* | 7/2004 | Tenengauzer et al. | 514/29 |

FOREIGN PATENT DOCUMENTS

| | | |
|---|---|---|
| EP | 0307128 | 8/1988 |
| EP | 0679400 | 4/1995 |
| EP | 0758549 | 2/1997 |
| WO | WO 9530422 | 11/1995 |
| WO | WO 9912552 | 3/1999 |
| WO | WO0057886 | 5/2000 |
| WO | WO 0057886 | 10/2000 |
| WO | WO 0209640 | 2/2002 |
| WO | WO 02094843 | 11/2002 |

OTHER PUBLICATIONS

Rouhi et al, "The Right Stuff", Chemical and Engineering News, Feb. 24, 2003, pp. 32-35.*

Sheth, B, Bandelin, Fred, Shangraw, Ralph, Compressed Tablets in *Pharmaceutical Dosage Forms: Tablets*, vol. 1, Lieberman, Herbert A. and Lachman, Leon, eds., Marcel Dekker, Inc., New York 1980, pp. 109-185.

Hiestand, H.E.N. and Smith, D.P., "Indices of Tableting Performance", Powder Technology, 38 (1994) 145-159.

*Tableting Specification Manual*, 4th Edition, AphA, Washing DC (1995) Figure 25, p. 51.

Watt, Peter Ridgway, *Tablet Machine Instrumentation in Pharmaceutics: Principles and Practice*, Halstead Press, John Wiley & sons, New York (1988) pp. 19-25; 429, 430, 434.

Banker, Gilbert S., "Tablets and Tablet Product Design", *Sprowl's American Pharmacy*, Seventh Edition, Dittert, Lewis W. ed., J.B. Lippincott Company, Philadelphia (1974) pp. 379-381.

Hiestand, E.N. and Wilcox, C.J., Some Measurements of Friction in Simple Powder Beds J. Pharm. Sci. 57 (1968) 1421-1427 (information on internal angle of friction).

Wells, James I., *Pharmaceutical Preformulation: The Physicochemical Properties of Drug Substances*, Halsted Press, John Wiley & Sons, New York (1988) pp. 209-214.

*Handbook of Powder Science and Technology*, Fayed, M.E. and Otten, L., eds., Van Nostrand Reinhold Co., New York (1984) pp. 262, 396-407.

Tan, S.B. and Newton, J.M., "Powder flowability as an indication of capsule filling performance", International Journal of Pharmaceutics, 61, (1990) 145-155.

Carr, Ralph L., Jr., "Evaluation Flow Properties of Solids" Chemical Engineering, Jan. 18, 1965, 163-168 (1965).

(Continued)

*Primary Examiner*—Eli Peselev
(74) *Attorney, Agent, or Firm*—Steve Zelson; David L. Kershner

(57) ABSTRACT

This invention relates to a pharmaceutical formulation, in the form of a tablet, sachet or powder for suspension dosage form, which comprises dry granulated particles of a non-dihydrate form of azithromycin and, optionally, one or more pharmaceutically acceptable excipients. Preferably, the pharmaceutical formulation is a tablet containing between about 40%, by weight, to about 90%, by weight, non-dihydrate azithromycin.

More preferably, the pharmaceutical formulation contains non-dihydrate azithromycin selected from the forms B, D, E, F, G, H, J, M, N, O, P, Q, R, or mixtures thereof.

Even more preferably, the invention relates to a pharmaceutical formulation wherein the dosage of azithromycin is 250 mgA, 500 mgA, 600 mgA or 1000 mgA.

The present invention further relates to a dry granulated azithromycin particle, comprising a form of azithromycin, selected from forms D, E, F, G, H, J, M, N, O, P, Q, R and mixtures of non-dihydrate forms, and at least one pharmaceutically acceptable excipient.

13 Claims, No Drawings

OTHER PUBLICATIONS

Cohard, C., Chulia, D., Gonthier, Y. and Verain, A., "A Correlation Between Flowability and Tapping Variation Rates of Powders", Int. J. Pharm. Tech. & Prod. Mfr., 6(3) 10-16 (1985).

H. Kibbe, ed., *Handbook of Pharmaceutical Excipients*, Third Edition, American Pharmaceutical Association, 2000 (Colloidal Silicon Dioxide, Croscarmellos Sodium, Lactose, monohydrate spray-dried, Magnesium Stearate, Microcrystalline Cellulose, Sodium Lauryl Sulfate, Talc).

Sucker H. et al., Pharmazeutische Technologies, 1991, Thienme Verlag, Stuttgrt, pp. 262-263.

List P. et al., Hagers Handbuch der pharmazeutischen Praxis, 1971, Springer Verlag, Berlin Heidelberg, p. 315.

* cited by examiner

DRY GRANULATED FORMULATIONS OF AZITHROMYCIN

BACKGROUND OF THE INVENTION

Dry granulation is a process in which granulates are formed by a compaction step that is followed by sizing the compacts into particles that can be processed easily. It is often used to improve flow properties and/or densify the formulation which can facilitate further manufacturing processes such as tableting, encapsulation and powder filling. The compacts are made directly from powder blends that usually contain an active ingredient and other excipients including a lubricant.

Pharmaceutical manufacturers prefer the use of dry granulation techniques to wet granulation methods because of shorter processing times and cost advantages. However, dry granulation is generally limited to those situations in which the drug or active ingredient has physical characteristics suitable for forming pharmaceutically acceptable granulations and dosage forms such as tablets.

The addition of at least one excipient to the formulation is generally required and will contribute to increasing the tablet size of the final product. As tablet size must be within certain parameters to function as a suitable dosage form, there is a limit beyond which increasing tablet size to accommodate increasing amounts of excipients to enhance compactability is not practical. As a result, manufacturers are often limited to using the dry granulation method for formulations containing a low dose of the active ingredient per compressed tablet such that the formulation may accommodate sufficient levels of excipient to make dry granulation practical.

In the development of pharmaceutical dosage forms, it is important to balance several different objectives. It is important to prepare a pharmaceutical dosage form as economically as possible. It would be desirable to have a simple production method comprising a few processing steps. The dosage form should also optimally make available the active compound contained therein to the patient. Further, the dosage form should be easy to swallow. Smaller dosage forms are better accepted by patients and increase patient compliance.

Tablets are typically formed by pressure being applied to the material to be tableted on a tablet press. A formulation must have good flow properties for precise volumetric feeding of the material to the die cavity and suitable compressibility, compactability, and ejection properties to form a tablet.

There are a number of tablet presses, each varying in productivity but similar in basic function and operation. All compress a tablet formulation within a die cavity by pressure exerted between two steel punches, a lower punch and an upper punch. Tablet presses are typically designed to have a hopper for holding and feeding the formulation, a feeding mechanism for feeding the formulation to the die cavity, provision for placement of punches and dies, and in rotary tablet presses a cam track for guiding the movement of the punches. Two types of tablet presses are the single station or single-punch press and the multistation rotary press. Some tablet presses provide longer dwell times than others, allowing increased bonding to occur. Other presses may provide precompression.

Azithromycin, which is also named 9-deoxo-9a-aza-9a-methyl-9a-homoerythromycin A, generally, is not considered to be amenable to the production of directly compressible tablets of azithromycin formulations.

It would be desirable to develop an azithromycin formulation that is amenable to form suitable granules by dry granulation methods or to form tablets, from these granules, that have acceptable hardness and friability.

SUMMARY OF THE INVENTION

This invention relates to a pharmaceutical formulation, in the form of a tablet, sachet or powder for suspension dosage form, which comprises dry granulated particles of a non-dihydrate form of azithromycin and, optionally, one or more pharmaceutically acceptable excipients. Preferably, the pharmaceutical formulation is a tablet containing between about 40%, by weight, to about 85%, by weight, non-dihydrate azithromycin.

More preferably, the pharmaceutical formulation contains non-dihydrate azithromycin selected from the forms B, D, E, F, G, H, J, M, N, O, P, Q, R, or mixtures thereof.

Even more preferably, the invention relates to a pharmaceutical formulation wherein the dosage of azithromycin is 250 mgA, 500 mgA, 600 mgA or 1000 mgA.

The present invention further relates to a dry granulated azithromycin particle, comprising a form of azithromycin, selected from forms D, E, F, G, H, J, M, N, O, P, Q, R and mixtures of non-dihydrate forms, and at least one pharmaceutically acceptable excipient.

DETAILED DESCRIPTION

In the specification and claims that follow, reference will be made to a number of terms which shall be defined to have the following meaning.

The term "dry granulation" means the process of blending bulk azithromycin with at least one excipient. The blend is then compressed, or compacted, to form a compressed material or "compact". This material is then broken apart to form granules by crushing, grinding or cutting into dry granulated particles. Optionally, the particles may be further processed. Crushing, grinding, or cutting processes involve an operation that reduces the size of the compressed material such as accomplished by milling or by other operations known to those skilled in the art.

A "compact" is a compressed material formed by processing azithromycin and optional excipients by slugging or by roller compaction.

"Bulk azithromycin", as used herein, means azithromycin particles without added excipients. In the present invention, bulk azithromycin may be milled or unmilled.

"Granules", or "dry granulated particles" are defined herein as particles containing azithromycin and at least one pharmaceutically acceptable excipient, that are formed by dry granulation means.

The term "pharmaceutically acceptable" means that which is generally safe, non-toxic and neither biologically nor otherwise undesirable and includes that which are acceptable for human pharmaceutical use as well as veterinary use.

"Non-dihydrate azithromycin" means all amorphous and crystalline forms of azithromycin including all polymorphs, isomorphs, clathrates, salts, solvates and hydrates of azithromycin other than form A, the dihydrate form of azithromycin (azithromycin dihydrate).

Non-dihydrate azithromycin includes a hygroscopic hydrate of azithromycin, as disclosed in U.S. Pat. No. 4,474,768, which is designated herein as "form B".

Preferably, azithromycin is present in several alternate crystalline non-dihydrate forms, including forms D, E, F, G, H, J, M, N, O, P, Q and R, which are disclosed in U.S. patent application Ser. No. 10/152,106, filed May 21, 2002, the teachings of which are incorporated herein, by reference, in their entirety.

Both Family I and Family II isomorphs are hydrates and/or solvates of azithromycin. The solvent molecules in the cavities have a tendency to exchange between solvent and water under specific conditions. Therefore, the solvent/water content of the isomorphs may vary to a certain extent. Forms B, F, G, H, J, M, N, O, and P belong to Family I azithromycin and belong to a monoclinic $P2_1$ space group with cell dimensions of a=16.3±0.3 Å, b=16.2±0.3 Å, c=18.4±0.3 Å and beta=109±2°. Forms D, E and R belong to Family II azithromycin and belong to an orthorhombic $P2_1 2_1 2_1$ space group with cell dimensions of a=8.9±0.4 Å, b=12.3±0.5 Å and c=45.8±0.5 Å. Form Q is distinct from Families I and II.

Form D azithromycin is of the formula $C_{38}H_{72}N_2O_{12}.H_2O.C_6H_{12}$ in its single crystal structure, being azithromycin monohydrate monocyclohexane solvate. Form D is further characterized as containing 2-6% water and 3-12% cyclohexane by weight in powder samples. From single crystal data, the calculated water and cyclohexane content of form D is 2.1 and 9.9%, respectively.

Form E azithromycin is of the formula $C_{38}H_{72}N_2O_{12}.H_2O.C_4H_8O$ being azithromycin monohydrate monotetrahydrofuran solvate. Form E is a monohydrate and mono-THF solvate by single crystal analysis.

Form G azithromycin is of the formula $C_{38}H_{72}N_2O_{12}.1.5H_2O$ in the single crystal structure, being azithromycin sesquihydrate. Form G is further characterized as containing 2.5-6% water and <1% organic solvent(s) by weight in powder samples. The single crystal structure of form G consists of two azithromycin molecules and three water molecules per asymmetric unit. This corresponds to a sesquihydrate with a theoretical water content of 3.5%. The water content of powder samples of form G ranges from about 2.5 to about 6%. The total residual organic solvent is less than 1% of the corresponding solvent used for crystallization.

Form H azithromycin is of the formula $C_{38}H_{72}N_2O_{12}.H_2O.0.5C_3H_8O_2$ being azithromycin monohydrate hemi-1,2 propanediol solvate. Form H is a monohydrate/hemi-propylene glycol solvate of azithromycin free base.

Form J azithromycin is of the formula $C_{38}H_{72}N_2O_{12}.H_2O.0.5C_3H_7OH$ in the single crystal structure, being azithromycin monohydrate hemi-n-propanol solvate. Form J is further characterized as containing 2-5% water and 1-5% n-propanol by weight in powder samples. The calculated solvent content is about 3.8% n-propanol and about 2.3% water.

Form M azithromycin is of the formula $C_{38}H_{72}N_2O_{12}.H_2O.0.5C_3H_7OH$, being azithromycin monohydrate hemi-isopropanol solvate. Form M is further characterized as containing 2-5% water and 1-4% 2-propanol by weight in powder samples. The single crystal structure of form M would be a monohydrate/hemi-isopropranolate.

Form N azithromycin is a mixture of isomorphs of Family I. The mixture may contain variable percentages of isomorphs, F, G, H, J, M and others, and variable amounts of water and organic solvents, such as ethanol, isopropanol, n-propanol, propylene glycol, acetone, acetonitrile, butanol, pentanol, etc. The weight percent of water can range from 1-5.3% and the total weight percent of organic solvents can be 2-5% with each solvent content of 0.5 to 4%.

Form O azithromycin is of the formula $C_{38}H_{72}N_2O_{12}.0.5H_2O.0.5C_4H_9OH$, being a hemihydrate hemi-n-butanol solvate of azithromycin free base by single crystal structural data.

Form P azithromycin is of the formula $C_{38}H_{72}N_2O_{12}.H_2O.0.5C_5H_{12}O$ being azithromycin monohydrate hemi-n-pentanol solvate.

Form Q azithromycin is of the formula $C_{38}H_{72}N_2O_{12}.H_2O.0.5C_4H_8O$ being azithromycin monohydrate hemi-tetrahydrofuran solvate. It contains about 4% water and about 4.5% THF.

Form R azithromycin is of the formula $C_{38}H_{72}N_2O_{12}.H_2O.C_5H_{12}O$ being azithromycin monohydrate mono-methyl tert-butyl ether solvate. Form R has a theoretical water content of 2.1 weight % and a theoretical methyl tert-butyl ether content of 10.3 weight %.

Form F azithromycin is of the formula $C_{38}H_{72}N_2O_{12}.H_2O.0.5C_2H_5OH$ in the single crystal structure, being azithromycin monohydrate hemi-ethanol solvate. Form F is further characterized as containing 2-5% water and 1-4% ethanol by weight in powder samples.

The single crystal of form F is crystallized in a monoclinic space group, $P2_1$, with the asymmetric unit containing two azithromycin, two waters, and one ethanol, as a monohydrate/hemi-ethanolate. It is isomorphic to all Family I azithromycin crystalline forms. The theoretical water and ethanol contents are 2.3 and 2.9%, respectively.

The term "mgA" refers to milligrams of the free base of azithromycin.

The term "blend", as used herein, means a generally homogeneous mixture of non-dihydrate azithromycin and at least one pharmaceutically acceptable excipient in particle form. The particles may be in powdered form or, alternatively, larger aggregated or agglomerated particles. The non-dihydrate azithromycin in a blend, of the present invention, is selected from azithromycin forms D, E, F, G, H, J, M, N, O, P, Q, R or mixtures of non-dihydrate forms.

The blend, of the present invention, is used to produce non-dihydrate azithromycin granules by dry granulation methods such as by compressing or compacting. Typically, blends of the present invention, include up to about 99 wt % non-dihydrate azithromycin, from about 0 wt % to about 90 wt % binder, from 0 wt % to about 85 wt % diluent, from 0 wt % to about 15 wt % disintegrant; and from about 0.25 wt % to about 10 wt % lubricant.

In a further embodiment, the dry blend contains up to about 80 wt % azithromycin, from about 2 wt % to about 10 wt % disintegrant, from about 0.5 wt % to about 8 wt % lubricant; and from about 0 wt % to about 85 wt % diluent.

Preferably, the azithromycin in the blend is azithromycin form F.

In the blend of the present invention, suitable pharmaceutically acceptable excipients include, but are not limited to, binders, diluents, disintegrants, lubricants, fillers, carriers, and the like.

Binders are used to impart cohesive qualities to a tablet formulation, and thus ensure that a tablet remains intact after compaction. Suitable binder materials include, but are not limited to, microcrystalline cellulose, gelatin, sugars (including sucrose, glucose, dextrose and maltodextrin), polyethylene glycol, waxes, natural and synthetic gums, polyvinylpyrrolidone, cellulosic polymers (including hydroxypropyl cellulose, hydroxypropyl methylcellulose, methyl cellulose, hydroxyethyl cellulose, and the like).

The diluent employed in a composition of the present invention may be one or more compounds which are capable of providing compactability and good flow. A variety of materials may be used as fillers or diluents. Suitable diluents or fillers include, but are not limited to, lactose (monohydrate, spray-dried monohydrate, anhydrous and the like), sucrose, dextrose, mannitol, sorbitol, starch, cellulose (e.g. microcrystalline cellulose; Avicel®), dihydrated or anhydrous dibasic calcium phosphate, calcium carbonate, calcium sulfate, and others as known in the art.

The preferred diluents are anhydrous lactose, lactose monohydrate and dibasic calcium phosphate. More preferably, the diluent is microcrystalline cellulose.

Many excipients, in the present invention, function as both a binder and a diluent, such a microcrystalline cellulose.

Lubricants can be employed herein in the manufacture of certain dosage forms, and will usually be employed when producing granules and tablets. In the present invention, a lubricant is typically added just prior to slugging or compacting to form the granule, and is mixed with the formulation for a minimum period of time to obtain good dispersal. The lubricant employed in the present invention may be one or more compounds. Examples of suitable lubricants include, but are not limited to, magnesium stearate, calcium stearate, zinc stearate, stearic acid, talc, glyceryl behenate, polyethylene glycol, polyethylene oxide polymers (for example, available under the registered trademarks of Carbowax™ for polyethylene glycol and Polyox™ for polyethylene oxide from Dow Chemical Company, Midland, Mich.), sodium lauryl sulfate, magnesium lauryl sulfate, sodium oleate, sodium stearyl fumarate, DL-leucine, colloidal silica, and others as known in the art. Preferred lubricants are magnesium stearate and mixtures of magnesium stearate with sodium lauryl sulfate. Lubricants may comprise from about 0.1 wt % to about 8.0 wt % of the granule weight.

Disintegrants are used to facilitate tablet disintegration or "breakup" after administration, and are generally starches, clays, celluloses, algins, gums or crosslinked polymers. Suitable disintegrants include, but are not limited to, crosslinked polyvinylpyrrolidone (PVP-XL), sodium starch glycolate, and croscarmellose sodium. If desired, the pharmaceutical formulation may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, sodium lauryl sulfate, dioctyl sodium sulfosuccinate, polyoxyethylene sorbitan fatty acid esters, etc.

To prepare the blend, the various components may be weighed, delumped and combined. The mixing may be carried out for a sufficient period of time to produce a homogeneous blend. Lubricant may be added in one, or multiple steps, prior to and/or after initial blending of the azithromycin and other excipients. Afterwards, the final mixing may be carried out. The blend may be stored for later use or formulated into a granule.

The components of the blend, including the non-dihydrate azithromycin and the excipient(s), may be combined by blending, mixing, stirring, shaking, tumbling, rolling or by any other methods of combining the formulation components to achieve a homogeneous blend. It is preferable that the azithromycin and excipients are combined under low shear conditions in a suitable apparatus, such as a V-blender, tote blender, double cone blender or any other apparatus capable of functioning under preferred low shear conditions. Lubricant is typically added in the last step.

The invention should not be considered limited to these particular conditions for combining the components and it will be understood, based on this disclosure that the advantageous properties can be achieved through other conditions provided the components retain their basic properties and substantial homogeneity of the blended formulation components of the formulation is otherwise achieved without any significant segregation.

In one embodiment for preparing the blend, the components are weighed and placed into a blending container. Blending is performed for a period of time to produce a homogenous blend using suitable mixing equipment. Optionally, the blend is passed through a mesh screen to delump the blend. The screened blend may be returned to the blending container and blended for an additional period of time. Lubricant may then be added and the blend mixed for an additional period of time.

The blend, of the present invention, is then compressed, or compacted, to form a compact. Prior to compression, the blend may be subjected to a precompression step such as on a rotary tablet press.

Compression of the blend to form granules may be accomplished by techniques known in the art including slugging where the blend is introduced into dies comprising one or more punch faces that are installed on a press such as a tablet press and pressure is applied to the blend by the movement of one or more punch faces in the die. Dry granulation may also be performed through the use of a roller compactor. A roller compactor generally incorporates two or more rollers adjacent and parallel to each other with a fixed or adjustable gap between the rollers. A hopper or other feeding device deposits blend between the moving rollers which act to compact the blend into a compacted material. Roller compactors are typically equipped with dividers that cut or otherwise divide the compacted material emerging from the roller compactor into ribbons. An example of a roller compactor is TF-Mini Roller Compactor (Vector Corporation, Marion, Iowa).

The compact is then broken apart to form granules, typically by suitable mechanical means, such as by crushing, grinding or cutting.

For example, granules may be formed from a compact by milling. Milling involves subjecting the granules to a shear force such that the desired particle size of the granulation is achieved. The milling step may range from an aggressive process where the particle size is reduced significantly to a non-aggressive process where the particle size is not reduced significantly, but merely done to delump or break up larger clumps of granulation.

In the pharmaceutical industry, milling is often used to reduce the particle size of solid materials. Many types of mills are available including pin mills, hammer mills and jet mills. One of the most commonly used types of mill is the hammer mill. The hammer mill utilizes a high-speed rotor to which a number of fixed or swinging hammers are attached. The hammers can be attached such that either the knife face or the hammer face contacts the material. As material is fed into the mill, it impacts on the rotating hammers and breaks up into smaller particles. A screen is located below the hammers, which allows the smaller particles to pass through the openings in the screen. Larger particles are retained in the mill and continue to be broken up by the hammers until the particles are fine enough to flow through the screen. The material may optionally be screened. In screening, material is placed through a mesh screen or series of mesh screens to obtain the desired particle size.

The non-dihydrate azithromycin granules, of the present invention, which contain an azithromycin form selected from forms D, E, F, G, H, J, M, N, O, P, Q, R or mixtures of non-dihydrate forms, are then used to form a pharmaceutical formulation which is typically in the dosage form of a tablet, a capsule, a sachet or a powder for suspension.

Alternately, a pharmaceutical formulation of the present invention, comprising a tablet, sachet or powder for suspension, may consist of dry granulated particles of azithromycin form B and, optionally, at least one pharmaceutically acceptable excipient. The azithromycin form B granules can be made by the methods described for making the non-dihydrate azithromycin granules of the present invention.

Optionally, prior to forming the dosage form, the azithromycin granules are extragranularly mixed with at least one additional pharmaceutically acceptable excipient, such as a processing aid (e.g., a lubricant or glidant) to form a pharmaceutical composition of the present invention. This pharmaceutical composition may then be tableted, encapsulated or packaged as a sachet or powder for oral suspension. Disintegrants, as are typically known in the art, and preferably as described herein, may also be added prior to tableting.

Flavors and coloring agents may be added, as excipients, intragranularly and/or extragranularly in the present invention.

Flavors incorporated in the composition may be chosen from synthetic flavor oils and flavoring aromatics and/or natural oils, extracts from plants leaves, flowers, fruits, and so forth and combinations thereof. These may include cinnamon oil, oil of wintergreen, peppermint oils, clove oil, bay oil, anise oil, eucalyptus, thyme oil, cedar leaf oil, oil of nutmeg, oil of sage, oil of bitter almonds, and cassia oil. Also useful as flavors are vanilla, citrus oil, including lemon, orange, grape, lime and grapefruit, and fruit essences, including apple, banana, pear, peach, strawberry, raspberry, cherry, plum, pineapple, apricot, and so forth. The amount of flavoring may depend on a number of factors including the organoleptic effect desired. Generally the flavoring will be present in an amount of from 0.5 to about 3.0 percent by weight based on the total dosage form weight, when a flavor is used.

Other excipients and coloring agents may also be added to azithromycin pharmaceutical formulations. Coloring agents include, but are not limited to, titanium dioxide and/or dyes suitable for food such as those known as F. D. & C, dyes, aluminum lakes and natural coloring agents such as grape skin extract, beet red powder, beta carotene, annato, carmine, turmeric, paprika, and so forth. A coloring agent is an optional ingredient in the compositions of this invention, but when used will generally be present in an amount up to about 3.5 percent based on the total dosage form weight.

In one embodiment, the pharmaceutical formulation is a dosage form containing an amount of azithromycin equivalent to about 250 mgA. In a further embodiment the dosage form contains an amount of azithromycin equivalent to about 500 mgA. In yet another embodiment, the dosage form contains an amount of azithromycin equivalent to about 600 mgA. In an alternate embodiment, the dosage form contains an amount of azithromycin equivalent to about 1000 mgA.

Preferably, tablets of the present invention contain from about 40 wt % to about 90 wt % azithromycin of the total tablet weight, preferably from about 45 wt % to about 80 wt % azithromycin, and even more preferably from about 50 wt % to about 70 wt % azithromycin; from about 0 wt % to about 60 wt % binder; from 0 wt % to about 60 wt % filler; from 0 wt % to about 15 wt % disintegrant; and from about 0.25 wt % to about 10 wt % lubricant.

Tablets may be prepared using standard tableting equipment known in the industry as a gravity fed process, and with equipment having means to force feed the pharmaceutical formulation.

Typical compacting techniques for the preparation of a tablet utilizes a piston like device with three stages in each cycle 1) filling (adding the constituents of the tablet to the compression chamber including granulate and any extragranularly added excipient(s)) 2) compaction (forming the tablet) and 3) ejection (removing the tablet). The cycle is then repeated. A representative tablet press is a MANESTY EXPRESS 20 rotary press, manufactured by Manesty Machines Ltd., Liverpool, England, and many others are available. The method as defined in this aspect of the invention is not limited to any particular equipment, however. The equipment may be gravity fed or it may utilize means to force feed the lubricated blend into the die.

In one embodiment, a high speed tablet press may be used. In a further embodiment, a single station tableting press may be used. Flow of the blend on high speed tablet presses is very important to good weight control of the tablet. The use of a force feeder often improves tablet weight control for poorer flowing blends. Another common feature of high speed tablet presses is the ability to use precompression. Precompression taps the blend when the die is full with blend before the final compression step forms the tablet.

Prior to tableting, additional lubricant may be mixed with the granules. Suitable lubricants are as previously described herein. Lubricants may comprise from about 0.5 wt % to about 10 wt % of the tablet weight, more preferably about 1.0 to about 8 wt %, and even more preferably from about 3 to about 7.5 wt %. Typically, the amount of lubricant used depends, in part, on the particular lubricant that is chosen.

Though generally not required with dry granulated tablets, in an alternate embodiment the dry granulated tablet may comprise an amount of glidant that is less than about 3% by weight, based on the tablet weight. In a further embodiment, the direct compression tablet may comprise an amount of glidant that is less than about 1% by weight, based on the tablet weight. In an even further embodiment, the tablet may comprise an amount of glidant that is less than about 0.5% by weight, based on the weight of the glidant.

Suitable glidants include magnesium trisilicate, powdered cellulose, starch, talc, tribasic calcium phosphate, stearate salts and colloidal silicon dioxide. Most preferred glidants are talc, magnesium stearate and colloidal silicon dioxide.

Blending of the azithromycin granules and optional additional excipient(s), including lubricant, may be accomplished by the methods previously described herein.

Tablets, of the present invention, typically exhibit acceptable physical characteristics including good friability and hardness. The resistance of a tablet to chipping, abrasion or breakage under conditions of storage and transportation depends on its hardness and friability.

Friability is a standard test known to one skilled in the art. Friability is measured under standardized conditions by weighing out a certain number of tablets (generally 20 tablets or less), placing them in a rotating Plexiglas drum in which they are lifted during replicate revolutions by a radial lever, and then dropped approximately 8 inches. After replicate revolutions (typically 100 revolutions at 25 rpm), the tablets are reweighed and the percentage of formulation abraded or chipped is calculated. The friability of the tablets, of the present invention, is preferably in the range of about 0% to 3%, and values about 1%, or less, are considered acceptable for most drug and food tablet contexts. Friability which approaches 0% is particularly preferred.

In the present invention, it was unexpectedly found that compacts, used to prepare granules, that were prepared from azithromycin form F, were physically harder than compacts made from other forms of non-dihydrate azithromycin. Thus, these azithromycin form F granules are preferred for preparing oral dosage forms such as tablets.

Further, it was found that dry granulated tablets, containing azithromycin form F granules, possess superior hardness and friability characteristics. Thus, tablets containing azithromycin form F are also preferred.

In the present invention, it was also unexpectedly found that tablets containing drug loadings of 40 wt % azithromycin or greater were more robust than tablets with drug loadings of less than 40 wt % azithromycin. Thus, it is also preferred that tablets contain from about 40 wt % to about 90 wt % non-dihydrate azithromycin.

The tablets, of the present invention, may be any shape as long as the tablet is in a form that it may be administered orally and is not prone to capping or exceeds the desired friability. The tablets may be round, oblong, thick or thin, large or small in diameter, flat or convex, scored or unscored, and imprinted. Typically, examples of tablet shapes include, but are not limited to, round, oval, modified oval or modified capsule shapes.

In one embodiment, the tablet may be a modified capsule shape containing about 250 mgA azithyromycin, about 450 mg total weight. In one embodiment, the dimensions of the aforementioned tablet are 0.26"×0.53". In a further embodiment, the tablet may be an oval shape containing about 500 mgA azithromycin, about 900 mg total weight. In one embodiment, the dimensions of the tablet are 0.33"×0.67". In an even further embodiment, the tablet may be a modified oval shape containing about 600 mgA, about 1070 mg total weight. In one embodiment, the dimensions of the aforementioned tablet are 0.41"×0.75". A reference to tablet shapes can be found in FIG. 25, page 51 of the *Tableting Specification Manual*, fourth edition, published by the American Pharmaceutical Association, Washington, D.C., 1995; incorporated herein by reference in its entirety.

Due to the tensile strength of azithromycin form F, it is preferred that tablets, of any shape, be made from azithromycin form F as compared to using other forms of non-dihydrate azithromycin.

The tablets comprising less than 40 wt % of non-dihydrate azithromycin forms, other than form F, based on the total weight of the tablet are preferably round to prevent tablet breakage.

If desired, the tablet may be coated. The reasons for coating a tablet may include masking the taste of the drug, making tablets easier to swallow, protection against chipping during packaging, a barrier for moisture or light to improve product stability, and enhancing product appearance or recognition.

The coating process may include the use of a coating solution or suspension, usually aqueous that has acceptable viscosity for spraying and properties for it to adhere to the surface of the tablet when applied. During the coating process, the coating solution or suspension is atomized into fine droplets that come into contact with the tablet. As the droplets dry, a film is formed on the tablet which is the coating. There are several types of coating equipment used to coat tablets. One type is the pan coater in which tablets are rotated in a pan and coating solution is applied to the tablets as tablets tumble in the pan. Another coating process involves suspending the tablets in a column of air while the coating solution is sprayed onto the tablet (fluid bed process). One example of this is the Wurster column coating process. The tablet may be coated by any known process and the manner of application is not limited to any particular equipment.

The tablet coating(s) may be a white or colored Opadry® (Colorcon, West Point Pa.) suspension or a clear Opadry® solution. Alternatively a typical coating formulation would consist of a film forming polymer(s) such as hydroxypropyl methylcellulose (HPMC), hydroxypropyl cellulose (HPC), polyvinyl pyrrolidone (PVP) with additional ingredients such as plasticizers, opacifiers, colorants, and antioxidants. Sugar coating could also be used.

The pharmaceutical formulations of the present invention may be used for the treatment of bacterial or protozoal infections. The term "treatment", as used herein, unless otherwise indicated, means the treatment or prevention of a bacterial or protozoal infection, including curing, reducing the symptoms of or slowing the progress of said infection.

As used herein, unless otherwise indicated, the term "bacterial infection(s)" or "protozoal infection(s)" includes bacterial infections and protozoal infections that occur in mammals, fish and birds as well as disorders related to bacterial infections and protozoal infections that may be treated or prevented by administering antibiotics such as the compound of the present invention. Such bacterial infections and protozoal infections and disorders related to such infections include, but are not limited to, the following: pneumonia, otitis media, sinusitis, bronchitis, tonsillitis, and mastoiditis related to infection by *Streptococcus pneumoniae, Haemophilus influenzae, Moraxella catarrhalis, Staphylococcus aureus,* or *Peptostreptococcus* spp.; pharynigitis, rheumatic fever, and glomerulonephritis related to infection by *Streptococcus pyogenes,* Groups C and G streptococci, *Clostridium diptheriae,* or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae*; uncomplicated skin and soft tissue infections, abscesses and osteomyelitis, and puerperal fever related to infection by *Staphylococcus aureus,* coagulase-positive staphylococci (i.e., *S. epidermidis, S. hemolyticus,* etc.), *Streptococcus pyogenes, Streptococcus agalactiae,* Streptococcal Groups C-F (minute-colony streptococci), *viridans streptococci, Corynebacterium minutissimum, Clostridium* spp., or *Bartonella henselae*; uncomplicated acute urinary tract infections related to infection by *Staphylococcus saprophyticus* or *Enterococcus* spp.; urethritis and cervicitis; and sexually transmitted diseases related to infection by *Chlamydia trachomatis, Haemophilus ducreyi, Treponema pallidum, Ureaplasma urealyticum,* or *Neisseria gonorroeae*; toxin diseases related to infection by *S. aureus* (food poisoning and Toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamrydia trachomatis, Neisseria gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium,* or *Mycobacteriurum intracellulare*; gastroenteritis related to infection by *Campylobacter jejuni*; intestinal protozoa related to infection by *Cryptosporidium* spp.; odontogenic infection related to infection by *viridans streptococci*; persistent cough related to infection by *Bordetella pertussis*; gas gangrene related to infection by *Clostridium perfringens* or *Bacteroides* spp.; and atherosclerosis related to infection by *Helicobacter pylori* or *Chlamydia pneumoniae.* Bacterial infections and protozoal infections and disorders related to such infections that may be treated or prevented in animals include, but are not limited to, the following: bovine respiratory disease related to infection by *P. haem., P. multocida, Mycoplasma bovis,* or *Bordetella* spp.; cow enteric disease related to infection by *E. coli* or protozoa (i.e., *coccidia, cryptosporidia,* etc.); dairy cow mastitis related to infection by *Staph. aureus, Strep. uberis, Strep. agalactiae, Strep. dysgalactiae, Klebsiella* spp., *Corynebacterium,* or *Enterococcus* spp.; swine respiratory disease related to infection by *A. pleuro., P. multocida,* or *Mycoplasma* spp.; swine enteric disease related to infection by *E.* coli, Lawsonia intracellularis, Salmonella, or Serpulina hyodyisinteriae; cow footrot related to infection by *Fusobacterium* spp.; cow metritis related to infection by *E. coli*; cow hairy warts related to infection by *Fusobacterium necrophorum* or *Bacteroides nodosus*; cow pink-eye related to infection by *Moraxella bovis*; cow premature abortion related to infection by protozoa (i.e. *neosporium*); urinary tract infection in dogs and cats related to infection by *E. coli*; skin and soft tissue infections in dogs and cats related to infection by *Staph. epidermidis*, *Staph. intermedius*, *coagulase* neg. *Staph.* or *P. multocida*; and dental or mouth infections in dogs and cats related to infection by *Alcaligenes* spp., *Bacteroides* spp., *Clostridium* spp., *Enterobacter* spp., *Eubacterium*, *Peptostreptococcus*, *Porphyromonas*, or *Prevotella*. Other conditions that may be treated by the compounds and preparations of the present invention include malaria and atherosclerosis. Other bacterial infections and protozoal infections and disorders related to such infections that may be treated or prevented in accord with the method and compositions of the present invention are referred to in J. P. Sanford et al., "The Sanford Guide To Antimicrobial Therapy," 26th Edition, (Antimicrobial Therapy, Inc., 1996).

The term "effective amount" means the amount of azithromycin which, when administered in—the present invention prevents the onset of, alleviates the symptoms of, stops the progression of, or eliminates a bacterial or protozoal infection in a mammal.

The term "mammal" is an individual animal that is a member of the taxonomic class Mammalia. The class Mammalia includes, for example, humans, monkeys, chimpanzees, gorillas, cattle, swine, horses, sheep, dogs, cats, mice and rats.

In the present invention, the preferred mammal is a human.

Typically, azithromycin, is administered in dosage amounts ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. The preferred dosage amount is from about 2 mg/kg/day to about 50 mg/kg/day.

The azithromycin may be administered orally, or by other known means for administering azithromycin.

Although the foregoing invention has been described in some detail for purposes of illustration, it will be readily apparent to one skilled in the art that changes and modifications may be made without departing from the scope of the invention described herein.

Exemplification

The present invention will be further illustrated by means of the following examples. It is to be understood, however, that the invention is not meant to be limited to the details described therein.

Excipients, used in the following examples, were obtained as follows.

Dicalcium phosphate anhydrous was obtained from Rhone-Poulenc Chemicals, Shelton, Conn.

Dicalcium phosphate dihydrate (Emcompress®) was obtained from Penwest Pharmaceuticals Co., Patterson, N.Y.

Spray-dried Lactose, monohydrate (Fast Flo®) was obtained from Foremost Farms, Rothschild Wis.

Lactose, anhydrous direct tableting grade was obtained from Quest, Norwich, N.Y.

Microcrystalline cellulose (Avicel® PH200) was obtained from FMC Biopolymer, Philadelphia, Pa.

Croscarmellose sodium (Ac-Di-Sol®) was obtained from FMC Biopolymer, Philadelphia, Pa.

Crospovidone (PVP-XL, Polyplasdone® XL),was obtained from International Specialty Products, Wayne, N.J.

Sodium starch glycolate (Explotab®) was obtained from Penwest Pharmaceuticals Co., Patterson, N.Y.

Corn Starch (Purity 21®) was obtained from National Starch & Chemical, Bridgewater, N.J.

Magnesium stearate was obtained from Mallinckrodt, Inc., St. Louis, Mo.

Sodium lauryl sulfate was obtained from Aceto Corporation, Lake Success, N.Y.

EXAMPLE 1

Indices of Tableting Performance

Indices of tableting performance, for several azithromycin forms, were assessed to identify any mechanical deficiencies or attributes that may affect tablet formulation for these azithromycin forms. This assessment was performed in accordance with the procedures described in "Indices of Tableting, Performance" H. E. N. Hiestand and D. P. Smith, Powder Technology 38 [1984] pp. 145-159.

Specifically, the Brittle Fracture Index, BFI, was calculated from the ratio of a material's regular tensile strength to its compromised tensile strength. Strain Index, SI, was determined from the dynamic indentation hardness test. Worst Case Bonding Index was determined by assessing the extent of particle bonding remaining after decompression assuming a very short compression dwell time and a plastic mechanism of particle separation during decompression.

Tableting Indices were determined for bulk azithromycin lots of six different crystalline forms, specifically forms N, M, G, A, F and J. Forms N, M and G were milled with a Fitzmill (Model JT, The Fitzpatrick Co., Elmhurst, Ill.) using a 0.027" screen and knives at high speed in an attempt to match the smaller particle size of milled Form A. Unmilled forms F and J were evaluated "as is" due to their relatively small particle sizes. The results of these assessments are shown in Table 1.

TABLE 1

Indices of Tableting Performance

| Azithromycin Form | Brittle Fracture Index (BFI) | Worst Case Bonding Index ($BI_w$) $\times 10^2$ | Strain Index (SI) | Tensile Strength Mpa |
|---|---|---|---|---|
| Form N | 0.05 | 0.7 | 0.0044 | 0.75 |
| Form M | 0.10 | 1.0 | 0.0048 | 0.79 |
| Form G | ND | 0.8 | 0.0043 | 1.03 |
| Form A | 0.10 | 0.9 | 0.0044 | 0.99 |
| Form F | 0.37 | 0.9 | 0.0041 | 1.62 |
| Form J | 0.11 | 0.7 | 0.0043 | 0.69 |

ND = not determined

As shown above, the tableting indices were similar for forms N, M, G, A and J. The data suggest that the primary deficiencies of these materials in forming compacts are their low to moderate tensile strengths. This may be manifested as low tablet hardness values. Furthermore, the brittle fracture indices indicated that bonds formed during compression will more likely survive decompression when the compact is ejected from the die. The differences between these lots were not significant. Thus, these lots would likely have a similar probability of forming acceptable tablet formulations.

Form F, however, exhibited significantly different mechanical properties. It had a higher tensile strength value indicative of forming stronger bonds. This resulted in tablets with higher hardness values and lower friability.

EXAMPLE 2

Dry Granulation of Azithromycin Forms

The impact of the blending process and the effect of azithromycin form on dry granulation was evaluated as follows.

Compacts (slugs) of azithromycin forms A, M and F formulations were prepared from a dry blend of 35.2 wt % azithromycin, 54.8 wt % dicalcium phosphate anhydrous as the diluent, 4.0 wt % croscarmellose sodium as the disintegrant, and 5.0 wt % magnesium stearate as the lubricant. The final 1.0 wt % magnesium stearate was added later just before tableting, for a total of 6.0 wt % lubricant.

The dry granulations were prepared by two different methods of blending. The long method blended 3 wt % of the lubricant with the drug, diluent and disintegrant in a Turbula Shaker-Mixer (Willy A. Bachofen AG Maschinenfabrik, Basel, Switzerland) mixer for 10 minutes. The blend was screened (20 mesh) and then blended another 10 minutes. An additional 2 wt % of lubricant was added and it was blended on the Turbula Shaker-mixer for 2 more minutes.

Alternatively a short blend method was used to minimize blend mixing with the lubricant. In this method the initial 10 minutes spent blending the drug, diluent, and disintegrant did not include the lubricant. After screening (20 mesh) and additional blending of 5 minutes, 5 wt % of the lubricant was added and blended for only 2 minutes in the Turbula Shaker-mixer.

A compaction simulator was used to compress the blends. The compaction simulator was designed as a single station tablet press in which the compression dwell time can be adjusted to simulate different types of tablet presses. All the formulations were slugged on the compaction simulator configured as the Kilian RX-67 press with a dwell time of 0.3145 seconds using ¾" round flat face tooling. The slugs were then comminuted using a Fitz mill with a 0.125" screen with knives forward and run at slow speed. The final amount of lubricant (1.0% magnesium stearate) was added to the dry granulation and blended for 2 minutes in the Turbula Shaker-mixer. The slugs were tested for hardness (kP scale), using a Schleuniger hardness tablet tester (Dr. Schleuniger Pharmatron AG, Solothurn, Switzerland). The results are shown in Table 2.

Carr's Compressibility Index was used to evaluate the flowability of the four dry granulations. Carr's Compressibility Index is a simple test to evaluate flowability by comparing both the initial and final (tapped) bulk volumes and the rate of packing down. A useful empirical guide to flow is given by Carr's compressibility index:

Compressibility Index(%)=[(tapped density−initial density)/tapped density]×100

The Carr's Compressibility Index was measured by taking an initial density of a 15 gram sample in a 100 ml graduated cylinder. The sample was tapped 2000 times on a VanKel Tap Density Tester (Model 50-1200, Edison, N.J.) and the tapped density of the 15 gram sample in the 100 ml graduated cylinder was taken. The procedure is described in *Int. J. Pharm. Tech. & Prod. Mfr.*, 6(3) 10-16, 1985. The results are provided in Table 2.

TABLE 2

| Summary of Dry Granulations | | | | |
|---|---|---|---|---|
| Lot # | 1 | 2 | 3 | 4 |
| Drug Form | A | F | A | M |
| Blend method | Long | Long | Short | Short |
| Dry Blend density (g/cc) | | | | |
| As Is | 0.59 | 0.50 | 0.59 | 0.68 |
| Tapped | 1.05 | 0.88 | 1.04 | 1.08 |
| Carr's Index | 44% | 43% | 43% | 36% |
| Avg Slug Weight | 1480 mg | 1499 mg | 1495 mg | 1506 mg |
| Slug Compression Force | 40 kN | 42 kN | 39 kN | 43 kN |
| Avg Slug Hardness | 13.4 kP | 22.4 kP | 13.7 kP | 10.9 kP |
| Avg Slug Thickness | 0.132" | 0.133" | 0.134" | 0.137" |
| Granulation density (g/cc) | | | | |
| As Is | 0.88 | 0.84 | 0.78 | 0.82 |
| Tapped | 1.19 | 1.07 | 1.14 | 1.14 |
| Carr's Index | 26% | 22% | 32% | 28% |

The dry granulations prepared by the long blend method resulted in good flow as shown by Carr's Index values of less than 28. The shorter blend method produced granules with poorer flow, having higher Carr's Index values.

All four formulations were compressed on the compaction simulator using either 0.344"×0.688" oval tooling, or ½" standard round concave (SRC) tooling. The tablets were tested for hardness (kP scale), using a Schleuniger hardness tablet tester (Dr. Schleuniger Pharmatron AG, Solothurn, Switzerland), and for friability (100 rotations/4 minutes) using a Vanderkamp Friabulator Tablet Tester (Vankel, Cary, N.C., US). The tests results are provided in Tables 2A and 2B.

TABLE 2A

| Summary of Dry Granulation Tablet Data Using the Long Blend Method | | | |
|---|---|---|---|
| Run # | 1 | 2 | 3 |
| Lot # | 1 | 1 | 2 |
| Drug Form | A | A | F |
| Blend method | Long | Long | Long |
| Tooling | Oval | ½" SRC | Oval |
| Dwell Time (sec) | 0.1153 | 0.1153 | 0.1153 |
| Avg Tab Weight | 751 mg | 747 mg | 750 mg |
| Compression Force | 13.5 kN | 9.6 kN | 19 kN |
| Avg Tablet Hardness | 9.0 kP | 5.8 kP | 10.3 kP |
| Avg Tablet Thickness | 0.202" | 0.195" | 0.201" |
| Friability | 2 of 5 tablets broke | 1.30% | 0.48% |
| Mean disintegration Time (sec) | 15 | NR | 20 |

NR = Not Run

TABLE 2B

| Summary of Dry Granulation Tablet Data Using the Shorter Blend Method | | | | |
|---|---|---|---|---|
| Run # | 4 | 5 | 6 | 7 |
| Lot # | 3 | 3 | 4 | 4 |
| Drug Form | A | A | M | M |
| Blend method | Short | Short | Short | Short |
| Tooling | Oval | Oval | Oval | Oval |
| Dwell Time (sec) | 0.1153 | 0.1153 | 0.1153 | 0.1153 |

TABLE 2B-continued

Summary of Dry Granulation Tablet Data
Using the Shorter Blend Method

| Avg Tab Weight | 752 mg | 749 mg | 749 mg | 749 mg |
|---|---|---|---|---|
| Compression Force | 12 kN | 18.7 kN | 19.4 kN | 14 kN |
| Avg Tab Hardness | 6.8 kP | 8.2 kP | 8.4 kP | 5.1 kP |
| Avg Tab Thickness | 0.204" | 0.201" | 0.204" | 0.208" |
| Friability | tablets capped | tablets capped | tablets capped | tablets capped |

The better tablets, made from azithromycin Form A, were compressed using a ½ inch SRC tooling (Run #2). The oval shaped tablets broke during friability testing.

Using azithromycin form F (Run #3), good oval shaped tablets were made. As shown in Example 1 the tableting indices data indicated that Form F has better tensile strength than Forms A and M. Both the Form F slugs and tablets were harder.

The disintegration time was determined in distilled water at 37° C. using an Automatic Disintegration Tester (Model ZT72, Erweka USA Inc, Milford, Conn.) for the long blend tablets. Even with extensive blending times with magnesium stearate, reasonably short disintegration times of 15 and 20 seconds were obtained.

Based upon the lower Carr's Index, the long blend method was used for the following examples.

EXAMPLE 3

Effect of Azithromycin Form and Low and High Drug Loading

The effects of drug form on dry granulation tablets were investigated using low and high drug loading formulations with forms A, F, J, and M. The long blend method and testing procedures as set forth in Example 2 were used.

The low drug loading formulation contained 35.2 wt % azithromycin, 54.8 wt % dicalcium phosphate anhydrous, 4.0 wt % croscarmellose sodium, and 6.0 wt % magnesium stearate. The high drug loading formulation contained 58.2 wt % azithromycin, 31.8 wt % dicalcium phosphate anhydrous, 4.0 wt % croscarmellose sodium, and 6.0 wt % magnesium stearate.

Slugs were made and tested for hardness (kP scale) as described in Example 2. The results for the low and high drug loading granulations are shown in Tables 3A and 3B, respectively.

The target hardness of ~12 kP was obtained with a much lower compaction force for the higher drug loading formulations indicative of the binding properties of the bulk drug. Form F had even greater binding properties as was shown by the tensile strength in Example 1. The low drug loading slugs made with comparable compression force were harder for form F than with the other forms, A, J and M. Carr's Index was used to evaluate the flowabilty of the granulations. All granulations had a Carr's Index value of 30% or less providing acceptable flow on a tablet press.

TABLE 3A

Summary of Low Drug Loading Dry Granulations

| Lot # | 1 | 2 | 3 | 4 |
|---|---|---|---|---|
| Drug Form | A | F | J | M |
| Avg Slug Weight | 1480 mg | 1499 mg | 1500 mg | 1506 mg |
| Avg Slug Compression Force | 39 kN | 42 kN | 41 kN | 43 kN |
| Avg Slug Hardness | 13 kP | 22 kP | 14 kP | 11 kP |
| Avg Slug Thickness | 0.132" | 0.131" | 0.134" | 0.138" |
| Granulation Density (g/cc) | | | | |
| As Is | 0.89 | 0.84 | 0.87 | 0.82 |
| Tapped | 1.19 | 1.08 | 1.12 | 1.14 |
| Carr's Index | 26% | 22% | 22% | 28% |

TABLE 3B

Summary of High Drug Loading Dry Granulations

| Lot # | 1 | 2 | 3 |
|---|---|---|---|
| Drug Form | A | J | M |
| Avg Slug Weight | 1498 mg | 1501 mg | 1501 mg |
| Avg Slug Compression Force | 28 kN | 18 kN | 22 kN |
| Avg Slug Hardness | 12 kP | 11 kP | 12 kP |
| Avg Slug Thickness | 0.156" | 0.197" | 0.191" |
| Granulation Density (g/cc) | | | |
| As Is | 0.67 | 0.67 | 0.71 |
| Tapped | 0.96 | 0.93 | 0.92 |
| Carr's Index | 30% | 28% | 23% |

The dry granulations were compressed into tablets on the compaction simulator using oval shaped (0.344"×0.688" punches, target weight 750 mg) tooling for the low drug loading formulations and a modified capsule shape (0.262"× 0.531" punch, target weight 450 mg) tooling for the high drug loading formulations. Tablet hardness and friability data were generated for the tablets as was done in Example 2. The tablet data are provided in Tables 3C and 3D for the low and high drug loading formulations, respectively.

TABLE 3C

Summary of Low Drug Loading Dry Granulation Tablet Data

| Lot # | 1 | 2 | 3 | 4 |
|---|---|---|---|---|
| Drug Form | A | F | J | M |
| Avg Weight (mg) | 751 | 748 | 747 | 749 |
| Avg Compresssion Force | 14 kN | 19 kN | 15 kN | 19 kN |
| Avg Hardness (kP) | 9.0 | 10.3 | 9.1 | 8.4 |
| Avg Thickness (in) | 0.202 | 0.201 | 0.201 | 0.204 |
| Friability (%) | Broken tablets | 0.48 | Broken tablets | NR |

NR = Not Run

TABLE 3D

Summary of High Drug Loading Dry Granulation Tablet Data

| Lot # | 1 | 2 | 3 |
|---|---|---|---|
| Drug Form | A | J | M |
| Avg Weight (mg) | 448 | 452 | 452 |
| Avg Compresssion | 5 kN | 4 kN | 5 kN |

TABLE 3D-continued

Summary of High Drug Loading Dry Granulation Tablet Data

| Force | | | |
|---|---|---|---|
| Avg Hardness (kP) | 6.2 | 6.5 | 6.1 |
| Avg Thickness (in) | 0.218 | 0.229 | 0.225 |
| Friability (%) | 0.50 | 0.38 | 0.45 |

As shown in Table 3C, the oval shaped tablets made with drug forms A and J broke during friability testing. The low drug loading formulation with drug form F showed good tablet friability and hardness consistent with its better tensile strength. All of the modified capsule shaped tablets made with the high drug loading granulations resulted in acceptable tablet hardness and good tablet friability as shown in Table 3D.

EXAMPLE 4

Effect of Different Diluents on Dry Granulation Tablets

The effect of different diluents on dry granulation tablets was investigated with both low and high drug loading formulations. Azithromycin forms A, F, G, and M were blended with diluents, dicalcium phosphate(DCP) anhydrous, dicalcium phosphate(DCP) dihydrate (Emcompress®), lactose (Fast Flo®), and microcrystalline cellulose (MCC)(Avicel® PH200). The same long blend method and testing procedures as set forth in Example 2 were used.

The low drug loading formulation contained 35.2 wt % azithromycin, 54.8 wt % diluent, 4.0 wt % croscarmellose sodium, and 6.0 wt % magnesium stearate. The high drug loading formulation contained 58.2 wt % azithromycin, 31.8 wt % diluent, 4.0 wt % croscarmellose sodium, and 6.0 wt % magnesium stearate. Slugs were made and tested for hardness (kP scale), as described in Example 2. The results for the low and high drug loading granulations are shown in Tables 4A and 4B, respectively. The Carr's Index was less than or equal to 30% for all the granulations. DCP dihydrate resulted in the lowest values, followed by MCC; while DCP, anhydrous and lactose were comparable.

TABLE 4A

Summary of Low Drug Loading Dry Granulations made with Different Diluents

| Lot # | 1 | 2 | 3 | 4 |
|---|---|---|---|---|
| Drug Form | A | A | G | M |
| Diluent | DCP, anhyd. | DCP, dihyd. | MCC | Lactose |
| Avg Slug Weight | 1480 mg | 1500 mg | 1503 mg | 1498 mg |
| Avg Slug Compression Force | 39 kN | 43 kN | 18 kN | 24 kN |
| Avg Slug Hardness | 13 kP | 11 kP | 13 kP | 13 kP |
| Avg Slug Thickness | 0.132" | 0.137" | 0.184" | 0.173" |
| Dry Granulation Density (g/cc) | | | | |
| As Is | 0.89 | 0.84 | 0.51 | 0.55 |
| Tapped | 1.19 | 1.04 | 0.68 | 0.78 |
| Carr's Index | 26% | 18% | 25% | 30% |

TABLE 4B

Summary of High Drug Loading Dry Granulations made with Different Diluents

| | Lot # | | | | |
|---|---|---|---|---|---|
| | 1 | 2 | 3 | 4 | 5 |
| Drug Form | A | A | G | M | F |
| Diluent | DCP, anhyd. | DCP, dihyd. | MCC | Lactose | DCP, dihyd. |
| Avg Slug Weight | 1498 mg | 1501 mg | 1505 mg | 1502 mg | 1504 mg |
| Avg Slug Compression Force | 28 kN | 25 kN | 16 kN | 18 kN | 8 kN |
| Avg Slug Hardness | 12 kP | 10 kP | 9 kP | 11 kP | 9 kP |
| Avg Slug Thickness (in) | 0.156 | 0.160 | 0.191 | 0.185 | 0.180 |
| Dry Granulation Density (g/cc) | | | | | |
| As Is | 0.67 | 0.69 | 0.53 | 0.53 | 0.63 |
| Tapped | 0.96 | 0.92 | 0.71 | 0.75 | 0.86 |
| Carr's Index | 30% | 25% | 25% | 29% | 27% |

The low drug loading dry granulations were compressed into tablets (target weight 750 mg) on the compaction simulator using 0.344"×0.688" oval shaped tooling or ½" standard round concave (SRC) tooling. Alternatively the high drug loading dry granulations were compressed into tablets (target weight 450 mg) on the compaction simulator using 0.262"× 0.531" modified capsule shaped tooling. Tablet hardness and friability data were generated for the tablets as described in Example 2. The tablet data are provided in Tables 4C and 4D for the low and high drug loading formulations, respectively. All tablets in Table 4D had the modified capsule shape.

As was previously shown in Example 2, the oval tooling produced friable tablets with the low drug loading granulations. Acceptable tablets were made with the same low drug loading granulations using SRC tooling. All the high drug loading granulations made good modified capsule shaped tablets, having friability values less than or equal to 0.5%. The lowest friability values for both the low and high drug loading granulations were obtained with MCC and lactose.

TABLE 4C

Tablet Data Summary for Low Drug Loading Dry Granulations made with Different Diluents

| Lot # | 1 | 2 | 3 | 4 |
|---|---|---|---|---|
| Drug Form | A | A | G | H |
| Diluent | DCP, anhyd. | DCP, dihyd. | MCC | Lactose |
| Tooling Shape | Oval | Oval | Oval | Oval |
| Avg Tablet Weight (mg) | 751 | 751 | 748 | 751 |
| Compression Force | 14 kN | 10 kN | 7 kN | 7 kN |
| Avg Tablet Hardness (kP) | 9.0 | 6.8 | 6.1 | 7.0 |
| Avg Tab Thickness (in) | 0.202 | 0.206 | 0.260 | 0.252 |
| Friability (%) | Broken tablets | Broken tablets | 1.30 | Broken tablets |
| Tooling Shape | SRC (½") | SRC (½") | SRC (½") | SRC (½") |
| Avg Tablet Weight (mg) | 747 | 751 | 752 | 752 |
| Compression Force | 10 kN | 10 kN | 9 kN | 10 kN |
| Avg Tablet Hardness (kP) | 5.8 | 6.2 | 5.3 | 7.5 |

TABLE 4C-continued

Tablet Data Summary for Low Drug Loading Dry
Granulations made with Different Diluents

| | | | | |
|---|---|---|---|---|
| Avg Tab Thickness (in) | 0.195 | 0.198 | 0.243 | 0.236 |
| Friability (%) | 1.30 | 0.94 | 0.78 | 0.53 |

TABLE 4D

Tablet Data Summary for High Drug Loading Dry
Granulations made with Different Diluents

| | Lot # | | | | |
|---|---|---|---|---|---|
| | 1 | 2 | 3 | 4 | 5 |
| Drug Form | A | A | G | M | F |
| Diluent | DCP, anhyd. | DCP, dihyd. | MCC | Lactose | DCP, dihyd. |
| Avg Tablet Weight (mg) | 448 | 454 | 453 | 452 | 452 |
| Compression Force | 5 kN | 5 kN | 5 kN | 4 kN | 4 kN |
| Avg Tablet Hardness (kP) | 6.2 | 5.2 | 5.8 | 5.8 | 7.0 |
| Avg Tablet Thickness (in) | 0.218 | 0.222 | 0.250 | 0.248 | 0.229 |
| Friability (%) | 0.50 | 0.49 | 0.41 | 0.28 | 0.31 |

EXAMPLE 5

Effect of Different Disintegrants and Tooling Types

The effect of different disintegrants on dry granulation tablets was investigated with high drug loading formulations for 250 mgA, 500 mgA and 600 mgA doses using different modified capsule, oval and modified oval tablet tooling, respectively. Azithromycin form M was blended with disintegrants, sodium starch glycolate (Explotab) or crospovidone (PVP-XL)(Polyplasdone® XL). The same long blend method and testing procedures as set forth in Example 2 were used.

The high drug loading formulation contained 58.2 wt % azithromycin, 31.8 wt % dicalcium phosphate dihydrate, 4.0 wt % disintegrant and 6.0 wt % magnesium stearate. Slugs were made and tested for hardness (kP scale), as described in Example 2. The granulation results are shown in Table 5A. The two formulations resulted in good flowing dry granulations as indicated by Carr's Index values less than or equal to 26%.

TABLE 5A

Summary of High Drug Loading Dry Granulations made with
Different Disintegrants

| Disintegrant | Explotab | PVP-XL |
|---|---|---|
| Avg Slug Weight | 1499 mg | 1515 mg |
| Avg Slug Compression Force | 34 kN | 35 kN |
| Avg Slug Hardness | 12 kP | 13 kP |
| Avg Slug Thickness | 0.161" | 0.164" |
| Dry Granulation Density (g/cc) | | |
| As Is | 0.67 | 0.63 |
| Tapped | 0.91 | 0.84 |
| Carr's Index | 26% | 25% |

Tablets were made on the compaction simulator to cover the azithromycin doses of 250 mgA, 500 mgA and 600 mgA using the tablet weights of about 450 mg, 900 mg and 1080 mg, respectively. To accommodate the change in tablet weight, different sized tablet tooling were used: 0.262"×0.531 modified capsule for the 250 mgA dose, 0.330"×0.670" oval for the 500 mgA dose and 0.406"×0.750" modified oval for the 600 mgA dose. The tablet data are shown in Table 5B. Acceptable tablets were made with the 250 mg dose and tooling without precompression. The larger tablets were too friable when made without precompression. Acceptable tablets were made with the oval or modified oval toolings when precompression was used.

Precompression involves using slight pressure to tap down the granulation prior to the final compression step during the tableting process. The type of disintegrant used in the formulation had little impact on the compaction properties of the final tablet based on the 250 mgA tablet data.

TABLE 5B

| Disintegrant | Explotab | PVP-XL |
|---|---|---|
| Dose (mgA) | 250 | 250 |
| Tooling Shape | Modified Capsule | Modified Capsule |
| Precompression | No | No |
| Avg Weight (mg) | 451 | 450 |
| Avg Compresssion Force (ACF) | 5 kN | 5 kN |
| Avg Hardness (kP) | 4.5 | 4.9 |
| Avg Thickness (in) | 0.226 | 0.230 |
| Friability (%) | 0.33 | 0.25 |
| Dose (mgA) | 500 | 600 |
| Tooling Shape | Oval | Modified Oval |
| Precompression | No | No |
| Avg Weight (mg) | 899 | 1082 |
| ACF | 6 kK | 6 kN |
| Avg Hardness (kP) | 5.6 | 4.2 |
| Avg Thickness (in) | 0.280 | 0.282 |
| Friability (%) | 2.71 | 6.34 |
| Dose (mgA) | 500 | 600 |
| Tooling Shape | Oval | Modified Oval |
| Precompression | 3.5 kN | 1.5 kN |
| Avg Weight (mg) | 898 | 1082 |
| ACF | 9 kN | 12 kN |
| Avg Hardness (kP) | 7.4 | 9.2 |
| Avg Thickness (in) | 0.275 | 0.268 |
| Friability (%) | 0.50 | 0.34 |

EXAMPLE 6

Effect of Tablet Shape and Drug Loading

The effect of tablet shape on dry granulation tablets was investigated with both low and high drug loading formulations using azithromycin form J. Both formulations were formulated with the same ingredients; only the percentage of drug and diluent was changed in the two formulations. The long blend method and testing procedures, set forth in Example 2, were used.

The low drug loading formulation contained 35.2 wt % azithromycin, 54.8 wt % dicalcium phosphate anhydrous, 4.0 wt % croscarmellose sodium, and 6.0 wt % magnesium stearate. The high drug loading formulation contained 58.2 wt % azithromycin, 31.8 wt % dicalcium phosphate anhydrous, 4.0 wt % croscarmellose sodium, and 6.0 wt % magnesium stearate. Slugs were made as described in Example 2. The results for the low and high drug loading granulations are shown in Tables 6A. The Carr's Index was less than or equal to 28% for both granulations.

TABLE 6A

Summary of Azithromycin Form J Dry Granulations

| Drug Loading | Low | | High | |
|---|---|---|---|---|
| Avg Slug Weight | 1500 | mg | 1501 | mg |
| Avg Slug Compression Force | 41 | kN | 18 | kN |
| Avg Slug Hardness | 14 | kP | 11 | kP |
| Avg Slug Thickness | 0.134" | | 0.166" | |
| Dry Granulation Density (g/cc) | | | | |
| As Is | 0.87 | | 0.67 | |
| Tapped | 1.12 | | 0.93 | |
| Carr's Index | 22% | | 28% | |

Tablets were made on the compaction simulator using different shaped tablet tooling. Both the 0.344"×0.688" oval tooling and the 0.262"×0.531 modified capsule tooling were used for each formulation. Additionally the ½" standard round concave (SRC) tooling was used for the low drug loading formulation as described in Examples 2 and 4. The tablet data are shown in Table 6B.

The oval shaped tablets with the low drug loading formulation broke during friability testing. The round shaped ½" SRC tablets using the low drug loading formulation produced tablets with improved friability of 1.46%. The same low drug loading granulation resulted in acceptable modified capsule shaped tablets with good friability. The high drug loading granulation resulted in acceptable tablets for both the modified capsule shape and the oval shaped tablets. The results indicate that tablet shape can be an important consideration. When using the low drug loading formulation, the modified capsule shaped tablet was the most preferred shape, followed by the SRC tablet shape; the oval shaped tablets were the most friable.

By using a higher drug loading formulation, it was possible to produce an improved oval shaped tablet. The modified capsule shaped tablets had a lower friability value with the higher drug loading formulation, indicating that the higher percentage of azithromycin in the formulation improved the binding properties of the tablet.

TABLE 6B

Tablet Data Summary for Different Tablet Shapes

| Drug Loading | Low | High |
|---|---|---|
| Tooling Shape | Modified Capsule | Modified Capsule |
| Tooling Dimensions | 0.262" × 0.531" | 0.262" × 0.531" |
| Avg Weight (mg) | 450 | 452 |
| Avg Compression Force (ACF) | 9 kN | 4 kN |
| Avg Hardness (kP) | 6.9 | 6.5 |
| Avg Thickness (in) | 0.193 | 0.229 |
| Friability (%) | 0.52 | 0.38 |
| Tooling Shape | Oval | Oval |
| Tooling Dimensions | 0.344" × 0.688" | 0.344" × 0.688" |
| Avg Weight (mg) | 747 | 750 |
| ACF | 15 kN | 10 kN |
| Avg Hardness (kP) | 9.1 | 10.2 |
| Avg Thickness (in) | 0.201 | 0.234 |
| Friability (%) | Broken Tablets | 0.71 |
| Tooling Shape and Size | ½" SRC | |
| Avg Weight (mg) | 752 | |
| ACF | 9 kN | |
| Avg Hardness (kP) | 5.4 | |
| Avg Thickness (in) | 0.200 | |
| Friability (%) | 1.46 | |

EXAMPLE 7

Dry Granulation by Roller Compaction of Azithromycin

As an alternate process to slugging, a roller compaction study was performed to determine the effect of various roller compaction pressures on the dry granulation. The study also investigated the effect of drug forms on the roller compaction process.

A batch size of about 100 g was made for each high drug loading formulation containing 58.2 wt % azithromycin, 31.8 wt % dicalcium phosphate anhydrous, 4.0 wt % croscarmellose sodium, and 6.0 wt % magnesium stearate. The long blend method, set forth in Example 2, was used. Two different lots of form A were compacted using a Vector Roller Compactor (Model TF-Mini, Vector Corporation, Marion, Iowa) and were screened through a 20 mesh screen. The roller compaction parameters and the resulting dry granulation properties are shown in Table 7.

TABLE 7

Granulation Properties and Roller Compactor Parameters

| Lot # | 1 | 2 | 3 | 4 |
|---|---|---|---|---|
| Form A Lot | milled | milled | unmilled | unmilled |
| Dry Blend Density (g/cc) | | | | |
| As Is | 0.49 | 0.49 | 0.57 | 0.57 |
| Tapped | 0.92 | 0.92 | 1.01 | 1.01 |
| Carr's Index | 47% | 47% | 44% | 44% |
| Roller Compactor Parameters | | | | |
| Roll Pressure Setting | 850 psi | 300 psi | 500 psi | 300 psi |
| Roll Speed | 5 rpm | 5 rpm | 5 rpm | 5 rpm |
| Screw Feed | 7 rpm | 7 rpm | 7 rpm | 7 rpm |
| Screened through | #20 mesh | #20 mesh | #20 mesh | #20 mesh |
| Dry Granulation Density (g/cc) | | | | |
| As Is | 0.55 | 0.60 | 0.64 | 0.66 |
| Tapped | 0.91 | 0.90 | 0.92 | 0.92 |
| Carr's Index | 39% | 33% | 30% | 26% |

The Carr's Index values for the dry blend were extremely high, greater than 44%, indicative of poor flow. After roller compacting, the Carr's Index values were reduced, indicative of better flowing material. Lower roller compaction pressures resulted in lower Carr's Index values.

The roller compaction process was evaluated for four different azithromycin forms, A, G, M and N. A batch size of about 300 g was made for each high drug loading formulation containing 55.76 wt % azithromycin, 32.24 wt % lactose, anhydrous, 10.0 wt % corn starch, and 2.0 wt % magnesium stearate:sodium lauryl sulfate (9:1). The drug, lactose, and corn starch were passed through a #20 mesh screen and blended for 30 minutes in a Turbula Shaker-mixer. The dry blend was then passed through a #20 mesh screen and blended for another 30 minutes. Afterwards the dry blend was again passed through a #20 mesh screen, combined with 1.5 wt % of lubricant and blended for 5 minutes. The dry blend was roller compacted using a TF-Mini roller compactor (roller speed at 5 rpm, screw feed at 7 rpm, pressure of 850 psi). The compacted ribbons were passed through a #20 mesh screen. The screened granulation was blended for 15 minutes, another 0.5 wt % of lubricant was added and blended for an additional 5 minutes. The granulations were evaluated for flow using Carr's Index. All of the granulations had good flow; the Carr's Index values were less than or equal to 24%.

0 size capsule shells were filled with about 435 mg of the granulation by hand. Data for the dry granulations and the capsules are given in Table 7A.

TABLE 7A

Granulation and Capsule Properties

| Lot # | 1 | 2 | 3 | 4 |
|---|---|---|---|---|
| Drug Form | A | G | M | N |
| Roller Compactor Parameters | | | | |
| Roll Pressure Setting | 850 psi | 850 psi | 850 psi | 850 psi |
| Roll Speed | 5 rpm | 5 rpm | 5 rpm | 5 rpm |
| Screw Feed | 7 rpm | 7 rpm | 7 rpm | 7 rpm |
| Screened through | #20 mesh | #20 mesh | #20 mesh | #20 mesh |
| Dry Granulation Density (g/cc) | | | | |
| As Is | 0.66 | 0.67 | 0.62 | 0.65 |
| Tapped | 0.86 | 0.86 | 0.82 | 0.84 |
| Carr's Index | 24% | 22% | 24% | 23% |
| Avg. Capsule Fill Weight (mg) | 450.1 | 434.2 | 409.8 | 446.8 |

We claim:

1. A solid pharmaceutical formulation, comprising:
   a) dry granulated particles of a non-dihydrate form of azithromycin selected from the group consisting of substantially pure azithromycin monohydrate hemi-ethanol solvate and substantially pure azithromycin sesquihydrate; and
   b) optionally, one or more pharmaceutically acceptable excipients.

2. A pharmaceutical formulation of claim 1 wherein the non-dihydrate azithromycin comprises azithromycin monohydrate hemi-ethanol solvate.

3. A pharmaceutical formulation of claim 1 wherein the dosage of azithromycin is selected from the group consisting of 250 mgA, 500 mgA, 600 mgA and 1000 mgA.

4. A pharmaceutical formulation of claim 1 comprising a tablet containing between about 40%, by weight, to about 90%, by weight, non-dihydrate azithromycin.

5. A pharmaceutical formulation of claim 1 comprising a tablet containing between about 45%, by weight, to about 80%, by weight, non-dihydrate azithromycin.

6. A pharmaceutical formulation of claim 1 comprising a tablet containing between about 50%, by weight, to about 70%, by weight, non-dihydrate azithromycin.

7. A pharmaceutical formulation of claim 1, wherein said formulation is in the form of a tablet comprising
   (a) from about 40 wt % to about 90 wt % non-dihydrate azithromycin;
   (b) from about 0 wt % to about 60 wt % binder;
   (c) from 0 wt % to about 60 wt % filler;
   (d) from 0 wt % to about 15 wt % disintegrant; and
   (e) from about 0.25 wt % to about 10 wt % lubricant.

8. A pharmaceutical formulation in a tablet dosage form, wherein said tablet is produced by:
   (a) forming a blend of dry granulated particles of substantially pure non-dihydrate azithromycin and at least one pharmaceutically acceptable excipient; and
   (b) compressing said blend to form the azithromycin tablet; wherein said substantially pure non-dihydrate azithromycin is selected from the group consisting of forms azithromycin monohydrate hemi-ethanol solvate and azithromycin sesquihydrate.

9. A pharmaceutical formulation of claim 8 wherein the dosage of azithromycin is selected from the group consisting of 250 mgA, 500 mgA, 600 mgA and 1000 mgA.

10. A pharmaceutical formulation of claim 8 further comprising the step of precompressing said blend prior to compressing said blend to form the tablet.

11. A pharmaceutical formulation of claim 10 comprising a tablet containing between about 40%, by weight, to about 90%, by weight, non-dihydrate azithromycin.

12. A pharmaceutical formulation of claim 10 wherein the dosage of azithromycin is selected from the group consisting of 250 mgA, 500 mgA, 600 mgA and 1000 mgA.

13. A method of preparing an azithromycin pharmaceutical formulation, in a tablet comprising:
   a) forming a blend of substantially pure non-dihydrate azithromycin and at least one pharmaceutically acceptable excipient;
   b) compressing the blend to produce a compressed material;
   c) milling the compressed material to produce granules;
   d) processing the granules into a tablet;
   wherein said substantially pure non-dihydrate azithromycin is selected from the group consisting of azithromycin monohydrate hemi-ethanol solvate and azithromycin sesquihydrate.

* * * * *